US006585813B2

(12) United States Patent
Kiik et al.

(10) Patent No.: US 6,585,813 B2
(45) Date of Patent: Jul. 1, 2003

(54) SURFACE COVERING BUILDING MATERIALS RESISTANT TO MICROBIAL GROWTH STAINING

(75) Inventors: Matti Kiik, Richardson, TX (US); Michael L. Bryson, Blue Springs, AL (US); Casimir Paul Weaver, Northport, AL (US); Robert Eugene Pine, Garland, TX (US)

(73) Assignee: Elk Premium Building Products, Inc., Dallas, TX (US)

( * ) Notice: Subject to any disclaimer, the term of this patent is extended or adjusted under 35 U.S.C. 154(b) by 0 days.

(21) Appl. No.: 10/210,501

(22) Filed: Aug. 1, 2002

(65) Prior Publication Data

US 2003/0037698 A1 Feb. 27, 2003

Related U.S. Application Data

(63) Continuation of application No. 09/590,222, filed on Jun. 8, 2000, now abandoned.

(51) Int. Cl.⁷ ................. C09D 5/16; A01N 25/02; A01N 59/14; A01N 59/20; E04D 5/02
(52) U.S. Cl. .............. 106/18.3; 106/15.05; 106/281.1; 106/284.02; 52/518; 424/630; 424/650; 424/660; 428/144; 428/403; 428/489
(58) Field of Search ............... 106/15.05, 18.3, 106/281.1, 284.02; 428/144, 489; 424/630, 650, 660; 52/518

(56) References Cited

U.S. PATENT DOCUMENTS

| | | | |
|---|---|---|---|
| 3,197,313 A | 7/1965 | Griener ............... 106/15 |
| 3,484,267 A | 12/1969 | Sadler ............... 117/25 |
| 3,884,706 A | 5/1975 | Little ............... 106/15 |
| 3,886,021 A | 5/1975 | Breckenfelder ............... 156/246 |
| 3,888,176 A | 6/1975 | Horai, Jr. et al. ............... 106/15 |
| 3,888,682 A | 6/1975 | Nelson ............... 106/15 |
| 3,888,683 A | 6/1975 | Horai, Jr. et al. ............... 106/15 |
| 3,894,877 A | 7/1975 | Nelson ............... 106/18 |
| 3,932,143 A | 1/1976 | Marshall et al. ............... 29/195 |
| 4,082,885 A | 4/1978 | Rashid et al. ............... 428/281 |
| 4,092,441 A | 5/1978 | Meyer et al. ............... 427/37 |
| 4,193,898 A | 3/1980 | Miller ............... 260/23 |
| 4,405,680 A | 9/1983 | Hansen ............... 428/285 |
| 4,468,430 A | 8/1984 | Ruede ............... 428/291 |
| 4,521,333 A | 6/1985 | Graham et al. ............... 252/606 |
| 4,745,032 A | 5/1988 | Morrison ............... 428/215 |
| 4,784,897 A | 11/1988 | Brands et al. ............... 428/219 |
| 5,305,569 A | 4/1994 | Malmquist et al. ............... 52/309 |
| 5,356,664 A | 10/1994 | Narayan et al. ............... 427/186 |
| 5,382,475 A | 1/1995 | Kayser ............... 428/403 |
| 5,391,417 A | 2/1995 | Pike ............... 428/143 |
| 5,427,793 A | 6/1995 | Bigham et al. ............... 424/404 |
| 5,565,239 A | 10/1996 | Pike ............... 427/186 |
| 5,573,810 A | 11/1996 | Grubka ............... 427/186 |
| 5,599,586 A | 2/1997 | Israel ............... 422/299 |
| 5,666,776 A | 9/1997 | Weaver et al. ............... 52/557 |
| 5,743,985 A | 4/1998 | Ernest et al. ............... 156/243 |
| 5,965,257 A | 10/1999 | Ahluwalia ............... 428/357 |
| 6,156,289 A | 12/2000 | Chopra et al. ............... 423/633 |
| 6,176,920 B1 * | 1/2001 | Murphy et al. ............... 106/711 |
| 6,214,466 B1 | 4/2001 | Joedicke ............... 428/404 |
| 6,245,381 B1 | 6/2001 | Israel ............... 427/186 |

FOREIGN PATENT DOCUMENTS

JP       61-53371       *   3/1986

OTHER PUBLICATIONS

"Study of Algal Discoloration of Asphalt Roofing Shingles" 3M Industrial Mineral Products Division, St. Paul, Minnesota, Dec. 1987.

* cited by examiner

Primary Examiner—Anthony J. Green
(74) Attorney, Agent, or Firm—Baker Botts L.L.P.

(57) ABSTRACT

The present disclosure relates to surface covering building materials for roofs, sidewalls and other exterior surfaces exposed tb the weather such as, but not limited to, asphaltic and non-asphaltic roofing materials, wherein said surface covering building materials exhibit long-term resistance to microbial growth-induced staining. The surface covering building materials include a component having antimicrobial potential which consists essentially of (a) a copper component or a tin component and (b) a barium metaborate monohydrate component.

18 Claims, No Drawings

SURFACE COVERING BUILDING MATERIALS RESISTANT TO MICROBIAL GROWTH STAINING

This application is a continuation of U.S. patent application Ser. No. 09/590,222 of Kiik et al., filed Jun. 8, 2000, now abandoned, which is incorporated herein by reference.

FIELD OF THE INVENTION

The present invention relates to surface covering building materials for roofs, sidewalls and other exterior surfaces exposed to the weather such as, but not limited to, asphaltic roofing materials, non-asphaltic roofing materials and other exterior cladding building materials wherein said surface covering building materials exhibit resistance to microbial growth-induced staining thereon. The present invention further relates to methods of making these surface covering building materials.

BACKGROUND OF INVENTION

Since the conversion of roofing shingles from felt based substrates to fiberglass substrates, asphalt shingles have been increasingly vulnerable to staining from biological growth. Although biological growth-induced staining problems are more acute in warm, humid climates such as the Gulf Coast area of the Unites States, the problem exists in all moist climates. Roofing materials, such as shingles, frequently comprise a fiberglass substrate with a filled asphalt coating. The filler in the asphalt coating acts to make the roofing materials more fire resistant; but it has also been partly responsible for the increase in microbial growth-induced staining because the filler is often a flour-like substance (typically calcium carbonate—$CaCo_3$) which is conducive to microbial growth. Other filler materials besides calcium carbonate also support microbial growth.

Studies have shown that the organism responsible for the microbial growth-induced staining of roofing materials is primarily a cyanobacterium, formerly known as blue-green algae. See "Study of Algal Discoloration of Asphalt Roofing Shingles" 3M Industrial Mineral Products Division, St. Paul, Minn., December 1987. While the species of cyanobacterium may be different depending on the geographical location and environmental conditions, all of these organisms secrete a mucilaginous biofilm around their cells. This biofilm provides protection and a moisture reservoir for the cells of the organism and also contributes to the staining of roofing materials. Cyanobacteria need only indirect sun light, air, moisture and minute amounts of minerals to grow. Many asphaltic and non-asphaltic roofing materials provide sufficient nutrients and a habitable environment to support the growth of cyanobacteria.

Roofing materials generally must weather before the conditions become suitable for the establishment of microbial growth. Weathering occurs from UV degradation and washing from rain which causes the exposure of the filler and the deterioration (e.g. pitting, cracking) of the filled asphalt coating portion of the roofing material. The roughening of the filled asphalt coating, coupled with moisture from the dew or rain and the exposure of the filler, creates an environment for the attachment and growth of microbes, such as cyanobacterium.

The cement tile roofing industry has addressed the problem of microbial growth-induced staining by deferring the treatment to the after market roof cleaning industry which provides high pressure water cleaning systems incorporating chlorine bleach. In warm, humid climates, such cleaning may be required annually.

The Asphalt Roofing Manufacturers Association, on the other hand, suggests a cleaning procedure which comprises a gentle application of dilute chlorine bleach and trisodium phosphate to avoid roof damage, and cautions against high pressure water cleaning because this process can remove surface granules from asphaltic roofing-products and shorten roof life. See U.S. Pat. No. 5,599,586.

Roof material cleaning by gentle application of chlorine bleach and trisodium phosphate or by high pressure water cleaning is only temporarily effective however, and that effectiveness is minimal. To further address the problem, roofing material manufacturers have offered several types of microbial resistant products, but they have achieved limited success.

For instance, antimicrobial agents have been mixed with the granules which surface certain asphaltic roofing materials. U.S. Pat. No. 5,573,810 and U.S. Pat. No. 5,356,664 describe copper containing algae resistant granules which may be applied to the surface of an asphalt roofing material together with non-algae resistant granules. Similarly, U.S. Pat. No. 3,484,267 describes the application of zinc alloyed with another metal (e.g. copper, tin, lead, mercury, titanium, cadmium, boron, arsenic, selenium) to the surface of a roofing material either as an antimicrobial granule or as a weather corrodible strip. In U.S. Pat. No. 3,484,267, the roofing material to which the antimicrobial granule or weather corrodible strip is applied also comprises non-antimicrobial mineral granules substantially embedded in its surface. In addition, U.S. Pat. No. 5,382,475 describes three-layer ceramic-coated, algae-resistant roofing granules comprising a copper compound in the first two layers. The granules of U.S. Pat. No. 5,382,475 may be colored by adding a pigment to the third ceramic layer. Algicidal roofing granules are also described in U.S. Pat. No. 5,427,793 which discloses a roofing granule having an algicidal coating comprising an organic oil and a tin-acrylate polymer. The coating of the 5,427,793 patent may be applied to colored or non-colored granules. Similarly, U.S. Pat. No. 3,888,682, U.S. Pat. No. 3,888,683, U.S. Pat. No. 3,894,877 and U.S. Pat. No. 3,888,176 describe adding a metallic algicide to the heavy processing oils which are used in the post-treatment of color coated roofing materials. Furthermore, U.S. Pat. No. 3,884,706 discloses an algicidal roofing granule wherein copper and zinc are added to the color coating of a granule.

In addition, U.S. Pat. No. 5,599,586 describes the application of antimicrobial agents in the form of a polymer film, with improved weatherability, to the surface of roofing materials. However, surface application of antimicrobial metals is susceptible to the environment, and certain weather conditions such as rain can considerably shorten the residence time of such metals and limit the effectiveness of such methods.

Other methods to reduce the microbial growth-induced staining of asphaltic-based roofing materials have sought to address the problem by using a filler, which itself has antimicrobial properties. U.S. Pat. No. 5,391,417 describes a roofing material which includes a class F fly ash filler which has antimicrobial characteristics due to its acidity. While such fillers may address to some extent the problem of microbial growth induced staining of asphaltic-based roofing materials, they are limited to roofing materials comprising such fillers and thus cannot address the roofing material staining problem generally. In addition, class F fly ash filler is not fully effective on all the types of organisms that stain roofs (e.g. Florida filamentous-type cyanobacteria).

Methods to inhibit microbial growth-induced staining of non-asphaltic roofing materials have also been described. U.S. Pat. No. 3,197,313 describes adding an antimicrobial agent, barium metaborate monohydrate, throughout an asbestos-cement composite roofing material or to an asbestos-cement veneer which surfaces an asbestos cement composite roofing material. However, this method is also limited in that it only relates to asbestos-cement composite roofing materials which are no longer marketable due to the adverse medical conditions associated with asbestos. This method also requires significant amounts of the antimicrobial agent (e.g. at least 5% and preferably 10–15% by weight of the asbestos-cement product) which can be expensive.

Another method for inhibiting microbial growth-induced staining of non-asphaltic roofing materials has been described in U.S. Pat. No. 4,193,898. The patent discloses a protective covering for use such as in shingles and siding which comprises a resin, a plasticizer and vermiculite. The protective covering can further be made resistant to microbial growth by the addition of copper sulphate during the process of making the protective covering. The method of the patent is limited to only a particular type of roofing material, namely a non-composite non-asphaltic protective covering, and therefore, does not address the problem of microbial growth-induced staining in asphaltic or non-asphaltic roofing materials generally.

Thus, there is a need for long-term inhibition of microbial growth-induced staining of surface covering building materials which survives the weathering of the materials, which utilizes reduced quantities of a component having antimicrobial potential and which may be used with various types of surface covering building materials including, inter alia, asphaltic roofing materials, non-asphaltic roofing materials and other exterior cladding building materials. In addition, there is a need for an antimicrobial, colored roofing granule, which exhibits long-term inhibition of microbial growth-induced staining when applied to the surface of a surface covering building material.

SUMMARY OF THE INVENTION

The present invention provides surface covering building materials, such as, but not limited to, asphaltic roofing materials, non-asphaltic roofing materials and other exterior cladding building materials, with long-term resistance to microbial growth-induced staining thereon. The present invention also provides a method of making such surface covering building materials.

The surface covering building materials of the present invention, whether asphaltic or non-asphaltic, may include a filled portion having one or more components having antimicrobial potential wherein said component(s) are dispersed throughout said filled portion and wherein said component(s) provide long-term resistance to microbial growth by remaining present during the weathering process of the surface covering building material. For example, where the surface covering building material of the present invention is an asphaltic composite, such as an asphalt roofing shingle, the component having antimicrobial potential may be added to and dispersed throughout the filled asphalt-portion of the asphaltic composite surface covering building material. Alternatively, the component having antimicrobial potential may be added to any portion of the surface covering roofing materials of the present invention. For instance, when the surface covering building material of the present invention is non-asphaltic, such as, but not limited to, cement tile and composite imitation slate, the material may include one or more components having antimicrobial potential dispersed throughout any portion, including the entirety, of the non-asphaltic building material.

Whatever the type of surface covering building material, it may instead or additionally include a component(s) having antimicrobial potential on the surface of the building material wherein the component(s) provide long-term resistance to microbial growth by remaining present during the weathering of the material.

DETAILED DESCRIPTION

This invention is not limited to any particular surface covering building material and may confer microbial growth-induced stain resistance to a wide variety of such materials, including asphaltic and non-asphaltic surface covering building materials. Representative examples of such surface covering building materials include, inter alia, those surface covering building materials described in U.S. Pat. Nos. 3,886,021; 4,082,885; 4,405,680; 4,468,430; 5,305,569; 5,565,239; 5,666,776 and 5,743,985 which are incorporated herein by reference. The surface covering building materials may be in various forms including, for example, asphalt roofing shingles, non-asphaltic roofing shingles, roofing tiles, roll roofing, commercial cap sheets, modified bitumen cap sheets, shakes and sidewalls.

In one embodiment of the present invention, asphaltic and non-asphaltic surface covering building materials include a filled portion having one or more components having antimicrobial potential wherein the component(s) are dispersed throughout the filled portion and wherein the component(s) provide long-term resistance to microbial growth by remaining present during the weathering of the material. For example, where the surface covering building material of the present invention is an asphaltic composite, such as an asphalt roofing shingle, the component having antimicrobial potential may be added to and dispersed throughout the filled asphalt portion of the building material.

Alternatively, the component having antimicrobial potential may be added to any portion of the surface covering roofing materials of the present invention, including the entire material. For instance, surface covering building materials of the present invention may comprise, or additionally comprise, one or more components having antimicrobial potential on the surface of the filled portion of the material wherein said component(s) provide long-term resistance to microbial growth by remaining present during the weathering process of the material.

As used herein, long-term resistance to microbial growth-induced staining refers to resistance to such staining during the weathering of the surface covering building material for the normal life of the material (i.e. from about one to fifty, years).

The filled portion of the building material, as used herein, refers to any portion of a surface covering building material including a filler material known in the art including, inter alia, filler materials described in U.S. Pat. No. 5,965,257; U.S. Pat. No. 5,391,417 and U.S. Pat. No. 4,405,680, incorporated herein by reference.

In addition, the surface covering building material of the present invention may be non-asphaltic, such as, but not limited to, cement tile and composite imitation slate, and includes one or more components having antimicrobial potential dispersed throughout any portion, including the entirety, of the nonasphaltic building material. Whether asphaltic or non-asphaltic, the surface covering building material may instead or additionally comprise a component (s) having antimicrobial potential on the surface of such non-asphaltic building material wherein the component(s) provide long-term resistance to microbial growth by remaining present during the weathering process of the material.

Any suitable component having antimicrobial potential capable of withstanding the processing temperatures involved in making the asphaltic or non-asphaltic surface covering building materials may be employed in accordance with the present invention. As referred to herein, a component having antimicrobial potential is any component which can confer microbial growth-induced stain resistance to surface covering building materials including, inter alia, copper powder, copper flake, copper nitrate, copper oxide, copper sulfate, tin powder, tin sulfate, zinc oxide, zinc powder, zinc acetate, chromium oxide, barium salt, metallic salts, barium metaborate monohydrate, BULAB Flamebloc™ (also called Busan 11-M2# for fine grade and sold by Buckman Laboratories, Inc., Memphis, Tenn., JTM™ filler (JTM Industries, Kennesaw, Ga.), and Busan 11-M1™ (Buckman Laboratories, Inc., Memphis, Tenn.). An analysis of Bulab Flamebloc™ yielded the following information concerning its constituents:

|  | %/wt | Theoretical Percent As $BaBo_2$—$H_2O$ |
|---|---|---|
| Barium | 54.60 | 50.5 |
| Boron | 5.83 | 4.5 |
| Moisture | 7.05 | 18.0 |
| Silicone, As $SiO_2$ | 7.96 |  |
| Calcium, As CaO | 0.04 |  |
| Aluminum, As $Al_2O_3$ | 0.89 |  |
| Stontim, As SrO | 1.09 |  |
| Sodium, As $Na_2O$ | 0.94 |  |
| Sulfur, As $SO_4$ | 1.95 |  |
| Barium Metaborate Monohydrate (by difference) | 80.08% |  |

| Other | % wt |  | % wt |
|---|---|---|---|
| Phosphorous | <0.01 | Manganese | <0.01 |
| Tin | <0.01 | Iron | <0.01 |
| Thallim | <0.01 | Magnesium | <0.01 |
| Arsenic | <0.01 | Molybdenum | <0.01 |
| Selenium | <0.01 | Vanadium | <0.01 |
| Chromium | <0.01 | Silver | <0.01 |
| Antimony | <0.01 | Titanium | <0.01 |
| Potassium | <0.01 | Copper | <0.01 |
| Nickel | <0.01 | Zinc | <0.01 |
| Beryllium | <0.01 | Cadmium | <0.01 |
| Potassium | <0.01 | Lead | <0.01 |
| Cobalt | <0.01 | Bismuth | <0.01 |

In one embodiment, a copper component and a barium metaborate monohydrate component together comprise the component having antimicrobial potential. In a preferred embodiment, copper powder or copper flakes is the copper component and BULAB Flamebloc™ is the barium metaborate monohydrate component. In another embodiment, tin powder or tin sulfate and a barium metaborate monohydrate component together comprise the component having antimicrobial potential. The components having antimicrobial potential may be particulate and somewhat coarser than facial powder. The components having antimicrobial potential are preferably almost totally water insoluble and do not easily dissolve and wash away when exposed to the elements, particularly dew and rain. When dispersed throughout or added to the surface of the filled portion of the building material, the components having antimicrobial potential may be in particulate form or in dissolved liquid form. In the preferred embodiment, the components having antimicrobial potential are in particulate form.

BULAB Flamebloc™, which comprises 90% barium metaborate monohydrate, a known antimicrobial material, has resulted in superior and unexpected results when used together with copper powder or copper flakes in the surface covering building materials of the present invention.

The copper powder may be 100RXH (OMG Americas, Research Triangle Park, N.C.) where the particle size is typically:

| Sieve analysis: |  |
|---|---|
| +100 mesh | N |
| +150 mesh | 0.2% |
| +200 mesh | 17.4% |
| +325 mesh | 44.4% |
| −325 mesh | 38.0% |
| Chemical Analysis: | 99.87% copper |

The components having antimicrobial potential of the present invention preferably inhibit the growth of cyanobacterium when employed in the surface covering building materials of the present invention, and the components of the present invention also withstand high heat, mixing and abrasion without significantly losing their antimicrobial properties.

The components having antimicrobial potential may comprise from about 0.001% to about 10.0% of the surface covering building material of the present invention. Where multiple components with antimicrobial potential are employed, the total of the percentages for each component should remain within the preferred range. In a preferred embodiment, the component having antimicrobial potential comprises from about 0.05% to about 5.0% of the total surface covering building material of the present invention. In a particular preferred embodiment, about 0.25% of the filled portion comprises a copper component (e.g. copper powder or copper flakes) and about 0.25% of the filled portion comprises a barium metaborate monohydrate component (e.g. BULAB Flamebloc™, Busan 11-M1™, or Busan 11-M2™).

One method of making the surface covering building material of the present invention, whether asphaltic or non-asphaltic, comprises adding to a filled portion, during the surface covering building material making process, one or more components having antimicrobial potential wherein the component(s) are dispersed throughout the filled portion and wherein the component(s) provide long-term resistance to microbial growth by remaining present during the weathering of the material. The component having antimicrobial potential is added to the filled portion during the surface covering building material manufacturing process and therefore must withstand the heat of processing the material which ranges from about 50° C. to about 500° C. In a preferred embodiment, the method of making the asphaltic or non-asphaltic surface covering building materials of the present invention comprises dispersing throughout the filled portion between about 0.001% to about 10.0%, and preferably between about 0.05% to about 5.0%, of one or more components having antimicrobial potential, as defined herein, wherein the temperature of the filled portion is within the range from about 50° C. to about 500° C. and wherein the component having antimicrobial potential retains its antimicrobial potential.

The method of making a microbial growth-induced stain resistant surface covering building material comprising a filled portion may instead comprise, or additionally comprise, applying to the surface of said filled portion during the material making process one or more components having antimicrobial potential. For instance, when the building material is an asphaltic composite, application to the surface of the filled portion may be achieved by sprinkling or spraying the component having antimicrobial potential onto the surface while the filled asphalt portion of the roofing material is still hot.

For spraying or sprinkling onto the surface, any means which may facilitate application to the surface may-be used. Such means include, but are not limited to, using a metering feed screw or a vibrating feeder.

Another method of making the surface covering building material of the present invention, whether asphaltic or non-asphaltic, comprises adding to any portion, including the entire material, during the material making process, one or more components having antimicrobial potential wherein the component(s) are dispersed throughout the portion or the entire material and wherein the component(s) provide long-term resistance to microbial growth by remaining present during the weathering of the material. The components having antimicrobial potential are added to the material, or any portion thereof, during the material manufacturing process and therefore must withstand the heat of processing the material which ranges from about 50° C. to about 500° C. The method of making the surface covering building materials of the present invention comprises dispersing throughout the portion or the entire material between about 0.001% to about 10.0%, and preferably between about 0.05% to about 5.0%, of one or more components having antimicrobial potential, as defined herein, wherein the temperature of the material is within the range of about 50° C. to about 500° C. and wherein the component having antimicrobial potential retains its antimicrobial potential during such processing.

The method of making a microbial growth-induced stain resistant surface covering building material may instead comprise, or additionally comprise, applying to the surface of said material, or any portion thereof, during the material making process, while the material is still hot, one or more components having antimicrobial potential, wherein the component(s) having antimicrobial potential penetrate the surface of the material, or any portion thereof and provide resistance to microbial growth by remaining present during the weathering of the building material. Application to the surface of the material, or any portion thereof, may be achieved as described above for materials that include a filled portion.

The present invention also contemplates that after the component(s) having antimicrobial potential is added to the surface of any portion of the material, granules may then be added to the surface, as is usually done with roofing materials. For example, when the material is an asphaltic composite, granules may be added to the surface of the filled asphalt coating. During the process of adding the granules to the surface of the material, the component(s) having antimicrobial potential may enter part-way through the surface due to the weight of the granules and the force of the application as the granules are dropped onto the surface.

In addition, the applicants have discovered granules which themselves assist in imparting stain resistant characteristics to building materials. The colored granules of the present invention are used to coat surface covering building materials and include a paint film portion comprising one or more components having antimicrobial potential wherein said component(s) having antimicrobial potential are dispersed throughout the paint film and comprise from about 0.01% to about 20.0% and preferably from about 0.5% to about 10.0% of the paint film portion and wherein said component(s) provide resistance to microbial growth of said building material.

The method of making the colored granules of the present invention for use with surface covering roofing materials comprises adding to a paint film portion, during the granule making process, one or more components having antimicrobial potential wherein the components are dispersed throughout the paint film and wherein the components provide microbial growth resistance to the roofing material when added thereto. The component having antimicrobial potential is added to the paint film during the colored granule manufacturing process, and therefore must withstand the heat of firing the paint film onto the granules which may be as high as 600° C. In one embodiment, the colored granules include a component having antimicrobial potential which comprises a copper component (e.g. copper flakes or copper powder) and a barium metaborate monohydrate component (e.g BULAB Flamebloc™, Busan 11-M1™, or Busan 11-M2™). In another embodiment, the colored granules include a component having antimicrobial potential which comprises a tin component (e.g. tin powder) and a barium metaborate monohydrate component (e.g. BULAB Flamebloc™, Busan 11-M1™, or Busan 11-M2™).

The invention is further illustrated by reference to the following examples.

EXAMPLES

Example 1

Environmental Growth Tests With Shingles

A. Production of Roofing Shingles:

Hunt asphalt (Hunt Refinery, Tuscaloosa, Ala.) was mixed with Dolomite (a mixture of $CaCO_3$ and $MgCO_3$; Elk, Tuscaloosa, Ala.) to which 0.25% BULAB Flamebloc™ (Buckman Laboratories, Inc., Memphis, Tenn.) and 0.25% copper powder 100RXH (OMG Americas, Research Triangle Park, N.C.) had been added to provide a 65/35% filler to asphalt blend which then coated a fiberglass mat to provide asphalt shingle panels. A control blend which did not include any BULAB Flamebloc™ or copper powder was also prepared.

B. Composition of Shingles:

A typical 300 pound per square laminated shingle has the composition listed below in Table I.

TABLE I

| Component | Amount |
| --- | --- |
| Asphalt | 60.0lb. |
| Filler | 113.2lb. |
| Colored Granules | 67.4lb. |
| Fiberglass mat | 5.4lb. |
| Headlap | 37.9lb. |
| Backing | 13.6lb. |
| Sealant and Adhesive | 2.5lb. |
| Total Weight | 300.0lb. |

The copper powder, when added to the above components, replaces from between 0.001% to 10.0%, and preferably 0.25% (0.283 lb.) of the total filler content and the BULAB Flamebloc™ also replaces between 0.001% to 10.0%, and preferably 0.25% (0.283 lb.) of the total filler content. Therefore, a typical 300 lb. per square laminated shingle which includes copper powder and BULAB Flamebloc™ has the composition listed below in Table II.

TABLE II

| Component | Amount |
|---|---|
| Asphalt | 60.0 lb. |
| Filler | 112.634 lb. |
| Copper powder | 0.283 lb. |
| BULAB Flamebloc ™ | 0.283 lb. |
| Colored Granules | 67.4 lb. |
| Fiberglass mat | 5.4 lb. |
| Headlap | 37.9 lb. |
| Backing | 13.6 lb. |
| Sealant and Adhesive | 2.5 lb. |
| Total Weight | 300.0 lb. |

C. Growth of Organisms in media +/− dolomite filler:

BG-11 and Dolomite filler were placed in 25 cm$^2$ flasks with plug seal caps (Corning, Oneonta, N.Y.) to which was added either BULAB Flamebloc™ and/or copper powder at the percentages indicated below in Table III. Test organisms (stock=either cyanobacteria from shingles of Alabama, Arkansas, Georgia, Mississippi or Tennessee; or Florida derived cyanobacteria obtained from Florida shingles) were added into the flasks and allowed to grow for three months in the light on a white background. Between 10 to 21 tests were performed for each. Growth was assessed visually on a scale of 0 to 10, with 0 having no visual growth and 10 having as much or more growth as a control without copper or BULAB Flamebloc™. Table III indicates that copper powder and BULAB Flamebloc™ are able to inhibit the growth of both organisms, with copper powder being more effective than BULAB Flamebloc™ on the cyanobacteria stock and both having equivalent effects on the Florida organism. The addition of both copper powder and BULAB Flamebloc™ resulted in a greater reduction of growth of the Florida organism than either alone.

TABLE III

| Antimicrobial Component | Stock | Florida |
|---|---|---|
| 0.5% BULAB Flamebloc ™ | 3.7 | 2.0 |
| 0.5% Copper powder | 0.4 | 2.4 |
| 0.25% BULAB Flamebloc ™ + 0.25% Copper | 0.5 | 1.0 |

D. Comparative Testing of Shingle Panels:

Seven types of shingle panels were tested to determine the comparative microbial growth resistance of the panels. The results, as listed below in Table 1, demonstrate that the panels which included the combination of copper powder and BULAB Flamebloc™ had the least amount of microbial growth. The following is a description of the panels tested:
1. Control panels with no antimicrobial component added.
2. Panels wherein the antimicrobial agent was a first commercially available copper granule.
3. Panels wherein the antimicrobial agent was a second commercially available copper granule.
4. Panels wherein the antimicrobial agent was fly ash.
5. Panels wherein the antimicrobial agent was copper powder.
6. Panels wherein the antimicrobial agent was BULAB Flamebloc™.
7. Panels wherein the antimicrobial agent was copper powder +BULAB Flamebloc™.

The test panels were subject to controlled light cycling and water spraying which provided a tropical jungle-type environment. The shingle panels (2'×2') were sprayed with BG-11 media containing a stock organism (generated from cyanobacteria from shingles of either Alabama, Georgia, Mississippi, or Tennessee) and Florida-derived filamentous-type cyanobacteria (generated from organisms isolated from shingles of southern Florida). The number of panels exhibiting either visual or microscopic growth were indicated as shown in Table IV below.

TABLE IV

| Panel Description | Number of Panels | Visual Growth | Microscopic Growth |
|---|---|---|---|
| Control | 6 | 2 | 0 |
| First copper panels | 19 | 2 | 7 |
| Second copper panels | 5 | 3 | 0 |
| Fly ash filler panels | 5 | 1 | 2 |
| Copper powder panels | 1 | 0 | 1 |
| BULAB Flamebloc ™ panels | 1 | 0 | 1 |
| Copper powder + Flamebloc ™ panels | 1 | 0 | 0 |

Example 2

Composition of Colored Granules

The composition of one ton of finished, dry weight colored granules is listed in Table V below. The percentage of the antimicrobial agent is measured according to the paint film components which comprise the paint coating+the antimicrobial agent. Therefore, in Table V, the paint coating is 94.6%, the copper or tin component is 2.7% and the BULAB Flamebloc™ is 2.7% of the paint film.

TABLE V

| Component | Amount |
|---|---|
| Base material (rock or slag) | 1,900.0 lb. |
| Paint coating | 94.6 lb.* |
| Copper powder/flakes or tin powder | 2.7 lb. |
| BULAB Flamebloc ™ | 2.7 lb. |

*Note that the paint coatings may range from 20 lb. per ton to 250 lb. per ton for most colors.

The invention described and claimed herein is not to be limited in scope by the specific embodiments herein disclosed, because these embodiments are intended as illustrations of several aspects of the invention. Any equivalent embodiments are intended to fall within the scope of this invention. Indeed, various modifications of the invention in addition to those shown and described herein will become apparent to those skilled in the art from the foregoing description. Such modifications are also intended to fall within the scope of the following claims.

We claim:

1. A surface covering building material including a component having antimicrobial potential in an amount sufficient to resist microbial growth-induced staining of said material, which consists essentially of (a) a copper component selected from the group consisting of copper powder and copper flakes and (b) a barium metaborate monohydrate component.

2. The surface covering building material of claim 1 wherein the copper component comprises from about 0.001 to about 5.0% of the material.

3. The surface covering building material of claim 1 wherein the copper component comprises about 0.25% of the material.

4. The surface covering building material of claim 1 wherein the barium metaborate monohydrate component comprises from about 0.001 to about 5.0% of the material.

5. The surface covering building material of claim 1 wherein the barium metaborate monohydrate component comprises about 0.25% of the material.

6. A surface covering building material including a component having antimicrobial potential in an amount sufficient to resist microbial growth-induced staining of said material, said component consisting essentially of (a) a tin component selected from the group consisting of tin powder and tin sulfate and (b) a barium metaborate monohydrate component.

7. The surface covering building material of claim 1 or 6 wherein said material is selected from the group consisting of asphaltic roofing shingles, asphaltic rolled roofing, asphaltic roofing tiles, asphaltic commercial cap sheets, asphaltic sidewalls, non-asphaltic shingles, non-asphaltic rolled roofing, non-asphaltic roofing tiles, non-asphaltic commercial cap sheets and non-asphaltic sidewall.

8. The surface covering building material of claim 1 or 6 wherein the components are dispersed throughout the material.

9. The surface covering building material of claim 1 or 6 wherein the components are dispersed throughout a portion of the material.

10. The surface covering building material of claim 1 or 6 wherein the components are dispersed on the surface of the material.

11. The surface covering building material of claim 1 or 6 wherein the components are dispersed throughout the material and on the surface of the material.

12. The surface covering building material of claim 1 or 6 wherein the components are dispersed throughout a portion of the material and on the surface of the material.

13. The surface covering building material of claim 9 wherein said portion is a filled portion.

14. The surface covering building material of claim 12 wherein said portion is a filled portion.

15. A colored granule for surface covering building materials comprising a paint film portion which includes a component having antimicrobial potential in an amount sufficient to resist growth-induced staining of said material, which consists essentially of (a) a barium metaborate monohydrate component and (b) a component selected from the group consisting of copper powder, copper flakes, tin sulfate and tin powder.

16. The colored granule of claim 15 wherein the copper component comprises from about 0.01% to about 10.0% of the paint film portion.

17. The colored granule of claim 15 wherein the barium metaborate monohydrate component comprises from about 0.01% to about 10.0% of the paint film portion.

18. The colored granule of claim 15 wherein the tin component comprises from about 0.01% to about 10.0% of the paint film portion.

* * * * *